United States Patent [19]

Bowser et al.

[11] Patent Number: 5,019,140
[45] Date of Patent: May 28, 1991

[54] IRRADIATED EXPANDED POLYTETRAFLUOROETHYLENE COMPOSITES, AND DEVICES USING THEM, AND PROCESSES FOR MAKING THEM

[75] Inventors: John J. Bowser, Newark, Del.; Christopher T. Hyde, Lincoln University, Pa.

[73] Assignee: W. L. Gore & Associates, Inc., Newark, Del.

[21] Appl. No.: 287,811

[22] Filed: Dec. 21, 1988

[51] Int. Cl.$^5$ ............................................. B01D 19/00
[52] U.S. Cl. ........................................ 55/159; 55/485; 55/486; 55/524; 428/287; 428/480
[58] Field of Search ................... 55/159, 485–488, 55/524, 528; 428/286, 287, 480

[56] References Cited

U.S. PATENT DOCUMENTS

| | | | |
|---|---|---|---|
| 3,575,170 | 4/1971 | Clark | 55/159 |
| 3,778,971 | 12/1973 | Granger et al. | 55/159 |
| 3,854,907 | 12/1974 | Rising | 55/159 |
| 3,951,293 | 4/1976 | Schulz | 55/528 X |
| 3,993,566 | 11/1976 | Goldberg et al. | |
| 4,025,679 | 5/1977 | Denny | 55/528 X |
| 4,071,040 | 1/1978 | Moriarty | 55/524 X |
| 4,187,390 | 2/1980 | Gore | 55/528 X |
| 4,190,426 | 2/1980 | Ruschke | 55/528 X |
| 4,238,207 | 12/1980 | Ruschke | 55/159 |
| 4,276,170 | 6/1981 | Vaillancourt | 55/159 X |
| 4,324,574 | 4/1982 | Fagan | 55/528 X |
| 4,402,785 | 9/1983 | Withers | 156/499 |
| 4,427,425 | 1/1984 | Briggs et al. | 55/159 |
| 4,478,620 | 10/1984 | Tamura | 55/524 X |
| 4,525,182 | 6/1985 | Rising et al. | 55/159 |
| 4,767,426 | 8/1988 | Daly et al. | 55/487 |
| 4,774,001 | 9/1988 | Degen et al. | 55/528 X |
| 4,787,921 | 11/1988 | Shibata et al. | 55/159 |
| 4,816,328 | 3/1989 | Saville et al. | 55/524 X |
| 4,877,433 | 10/1989 | Oshitari | 55/528 X |

FOREIGN PATENT DOCUMENTS 0374605 12/1989 European Pat. Off. .
2737756 1/1979 Fed. Rep. of Germany .
2157188 10/1985 United Kingdom ................. 55/159

OTHER PUBLICATIONS

Chemical Engineering, J. S. Johnson, "Materials for Membranes", Aug. 1986; pp. 121–123.

Primary Examiner—Robert Spitzer
Attorney, Agent, or Firm—Gary A. Samuels

[57] ABSTRACT

Radiation resistant composites made of adjacent layers of a microporous hydrophobic polytetrafluoroethylene layer and one or more supporting layers made of woven metal material or woven synthetic organic polymeric material and a microporous hydrophobic polytetrafluoroethylene membrane are described. Filtration devices containing the composite are described.

14 Claims, 2 Drawing Sheets

IRRADIATED EXPANDED POLYTETRAFLUOROETHYLENE COMPOSITES, AND DEVICES USING THEM, AND PROCESSES FOR MAKING THEM

FIELD OF THE INVENTION

This invention relates to microporous hydrophobic composites that can be irradiated, as for example, to sterilize them, and still maintain their integrity under conditions of pressurization.

BACKGROUND

Polytetrafluoroethylene (PTFE) is a useful polymeric material that has found application in the construction of many devices which utilize its properties of inertness to chemical attack, hydrophobicity and biocompatibility. For example, it is used as a coating to protect chemical tanks which are used to hold corrosive chemicals; it is used as a moisture barrier in industrial applications to protect sensitive scientific instrumentation and also in rainwear garments; it is also used in biomedical applications for implantable devices such as vascular grafts and surgical patches.

A particularly useful form of PTFE is microporous PTFE. There are a number of ways to make microporous PTFE. One method is by an expansion process such as that described in U.S. Pat. No. 3,953,566. This patent describes a means of producing a microporous structure characterized by nodes connected by fibrils made by rapid expansion of PTFE. Another method is by a replication process such as that described in U.S. Pat. No. 3,497,256 which describes a means of sintering PTFE particles onto a fibrous substrate. Alternatively, microporous PTFE can be made by the removal of fugitive materials after extrusion as described in claim 1 of U.S. Pat. No. 4,613,544.

Microporous PTFE membranes are useful in a number of applications as either filters or venting barriers. These membranes are particularly useful materials in the design and construction of medical, pharmaceutical and other devices because they are hydrophobic materials which function as a barrier to liquid water and aqueous solutions or mixtures but because the membranes are microporous, they allow the flow of air or other gases and, if the pores are sufficiently small, they can be made to exclude microorganisms and other microscopic contaminants. These membranes and the devices constructed with these materials are commonly used in medical or pharmaceutical applications which require sterilization. There are a number of methods of sterilization which are used by manufacturers of such devices, including sterilization by steam, ethylene oxide gas, or ionizing radiation. The ionizing radiation can be of several types, such as, gamma irradiation or high energy electron beam bombardment, among others. There are significant economic and industrial hygiene advantages to using either gamma irradiation or electronbeam bombardment. However, while these methods of sterilization are more convenient, they also can cause more damage to the materials used in the device than the other means of sterilization. Although microporous PTFE exhibits extraordinary resistance to chemical attack from a wide variety of chemical species, it has only a very limited resistance to ionizing radiation. Microporous PTFE is particularly sensitive to degradation by ionizing radiation in comparison to other polymeric materials; it is usually rated as the polymeric material most susceptible to degradation by ionizing radiation. There is a need for a method by which microporous PTFE material can be used in applications which require or prefer the use of radiation sterilization and subsequent pressurization.

Specifically, the use of microporous PTFE in numerous applications is greatly limited by its marked susceptibility to the degradation of its physical properties such as ultimate tensile strength and ultimate elongation as the result of exposure to ionizing radiation. This decrease in physical properties is observed at relatively low levels of radiation; significant decreases are observed at radiation exposures of less than 0.5 Megarad. This radiation sensitivity imposes a serious limitation on the use of microporous PTFE in applications in which it is necessary for the material to withstand even relatively low levels of radiation. Gamma sterilization is generally accomplished by exposing the devices to be sterilized to 2.5 Megarad or more. An example of an application where radiation is typically encountered is medical or pharmaceutical devices which can be conveniently sterilized with ionizing radiation. It is necessary to use a dose of ionizing radiation sufficiently large to ensure that the article is completely sterile. This is commonly achieved by placing the articles to be sterilized in a shielded room with a relatively powerful irradiation source, such as a cobalt-60 source. The sources are usually of sufficient strength that the sterilization procedure can be accomplished in 60 to 120 minutes. The sterilization is normally performed after the microporous PTFE laminate has been incorporated into the device after the completion of all manufacturing steps. Another example is in space applications where the microporous PTFE is exposed to low doses of ionizing radiation for long periods of time.

This susceptibility to damage by ionizing radiation is particularly acute in applications which use thin sheets of PTFE and/or microporous or expanded PTFE. In these applications because of the limited amount of polymer which is present [as compared to devices which use thick pieces (e.g., slabs or rods) of full density PTFE, the decrease in the physical properties is often prohibitively detrimental. For many years this has prevented the use of microporous PTFE materials in applications which are sterilized with ionizing radiation.

This patent describes composites and devices which permit the use of thin sheets of microporous PTFE in those applications which require both sterilization with ionizing radiation and the ability to withstand sustained pressurization without rupturing or failing. Said composites and devices achieve greater than a one hundred fold increase in the useful lifetime with respect to existing laminates and devices.

SUMMARY OF THE INVENTION

Figure 1:
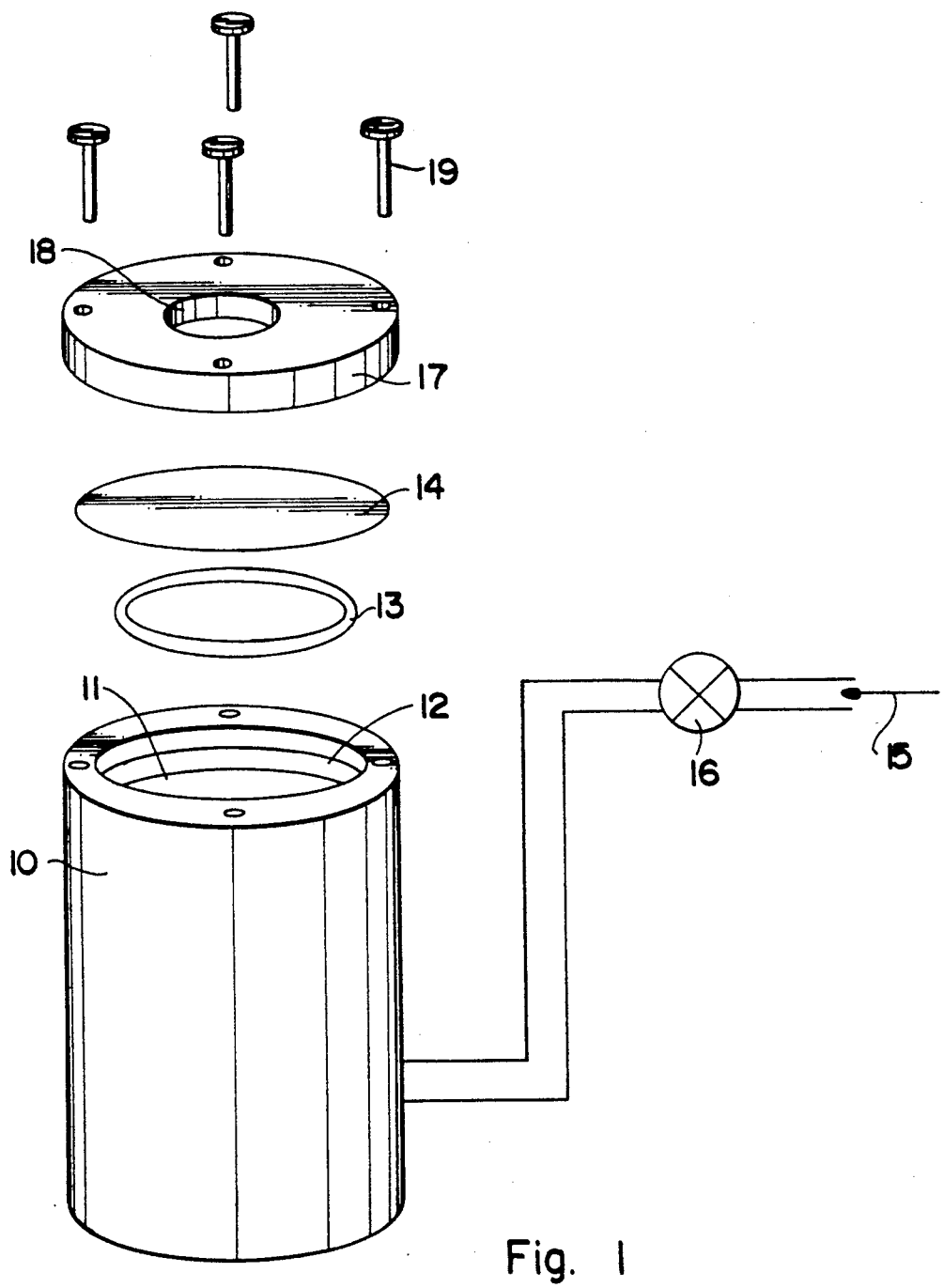
FIG. 1 is an exploded view of a Pressurization Test apparatus.

The composites and devices of the present invention achieve a one hundred fold increase in the useful lifetime of microporous membranes in irradiated composites and devices. Composites, as used herein, means a number of layers of material which may or may not be bonded to each other by an adhesive or other means of attachment. The present invention includes composites and devices which maintain the integrity of irradiated microporous hydrophobic membranes under conditions of pressurization. The composites contain supporting layers which prevent the transmission of excessive mechanical forces to the microporous membrane. The devices comprise the composite and means of restraint which provide strain relief at the supporting edges and the cross members to prevent the transmission of excessive mechanical forces to the membrane. The specific physical conditions which can cause the microporous membranes, and the commercially available composites containing them, to fail after exposure to ionizing radiation are 1) excessive elongation, 2) puncture on sharp protrusions and 3) concentration of stresses in limited areas.

Specifically, the composites of this invention comprise two or more layers of materials. When a two layer composite is made, the composite comprises:

(a) a layer of woven metal material or woven synthetic organic polymeric material having, after irradiation, an elongation of less than 25% after 100 hours under a load of 2.0 pounds per inch, and (b) a microporous hydrophobic polymeric membrane.

When a three layer composite is made, the composite comprises:

(a) a synthetic organic polymeric material having, after irradiation, an elongation of less than 25% after 100 hours under a load of 2.0 pounds per inch, (b) a compliant synthetic organic polymeric material, and (c) a microporous hydrophobic polymeric membrane. The properties of the various layers of the composites are such that the resulting composites are, after exposure to 5 Megarad of ionizing radiation, capable of withstanding 20 pounds per square inch gauge (psig) pressure for 100 hours in the Pressurization Test, described below. Some composites and devices, as described herein, achieve a one hundred fold increase in the useful lifetime of said irradiated microporous PTFE membranes.

The devices of this invention comprise the said laminates and the means of supporting the said laminates so as to provide strain relief at the edges of the body of the device and the supporting cross members.

The processes of the invention include a process for making the composites and a process for irradiating the unirradiated form of the composite.

DETAILED DESCRIPTION OF THE INVENTION

This invention comprises composites which include combinations of layers containing a microporous hydrophobic membrane, such as a microporous PTFE membrane, and includes laminates. The composites, or the devices incorporating them, can be exposed to ionizing radiation and used in applications which require that the membrane of the composite retain its integrity under brief or extended pressurization.

As used herein, the words "microporous hydrophobic membrane," or variations thereof, define those materials which have a surface free energy of less than 30 dyne/cm. and have nominal pore sizes in the range of about 0.01 to 100 micrometers. Such membranes prevent the passage of liquid water but allow the passage of air and other gases. This layer of the composite of the invention preferably has a thickness of 2 to 250 micrometers. Microporous hydrophobic membranes are made from a number of materials, for example polymers such as, but not limited to, PTFE, other perfluoropolymers, polyethylene or polypropylene, or the like. Alternatively, materials which are not hydrophobic can be modified to render their surfaces hydrophobic by methods such as solvent deposition, chemical vapor deposition or plasma polymerization or deposition of a thin layer of hydrophobic material.

As described previously, the composites include a number of layers arranged in a specified order; the layers may or may not be joined to each other by adhesive or other means of attachment, such as by encapsulation in the body of the device itself. The word "laminate" defines a species of composites which are joined to each other by some means of adhesion, such as hot melt bonding or solvent based adhesives. The words "combination of layers" define a species of composites in which the arrangement of the layers are maintained by other means of attachment, such as by encapsulation in the body of the device itself. The teachings of this patent apply to both laminates and unbonded combinations of layers; that is, it is obvious that improvements which are demonstrated with laminates can also be achieved with the corresponding unbonded combination of layers, and vice versa.

As used herein, the words "device", "filtration device", or variations thereof, defines any means by which the composite is restrained in a part, such as a plastic or metal cylinder, for the purposes of withstanding pressure and another function, such as filtering or venting. The composite may be restrained in place by a variety of means including, but not limited to, insert molding, overmolding, clamps, glue, gasket seals, or mechanical seals, such as, O-rings. The devices may be used for filtration, or other, purposes.

Composites containing microporous PTFE membranes fail when they are subjected to excessive conditions, that is, conditions which cause the materials (in particular, the microporous membrane) of construction to exceed their ultimate elongation limit and tensile strength. Exposure to ionizing radiation greatly reduces the ultimate elongation of microporous PTFE. Typically, the ultimate elongation of sheets of microporous PTFE is reduced from about 250% prior to irradiation to about 25% after exposure to 2.5 Megarad of gamma irradiation. This reduction in ultimate elongation represents the upper limit beyond which the membrane must not be stretched in the final application after exposure to ionizing radiation. Because irradiated microporous PTFE membranes are particularly susceptible to elongation failures, it is often advantageous to design in a certain margin of safety. This is demonstrated herein by testing the composites and devices at pressures two to fifty fold greater than pressures typically encountered in intravenous line administration sets.

Three conditions which will cause the membrane to rupture, that is, distend beyond its elongation limit, are pressure, duration of pressurization and the constraints of construction of the device containing the membrane or laminated membrane. First, when the membrane is subjected to pressures which cause it to distend beyond its ultimate elongation limit, the membrane will rupture and the barrier to aqueous passage will be broken. Second, when a membrane is subjected to pressures which are less than the immediate rupture pressure for a sustained period of time, the membrane may eventually fail after a prolonged period of time. Third, the actual pressure which causes the membrane in a device to fail is dependent on the design and construction of the device in which the membrane is tested or used. For example, constructions in which the membrane or laminate spans a large distance will fail at lower pressures or shorter times than a construction in which the membrane or laminate spans a smaller distance. These mechanical stresses can be cumulative. For example, the combination of high pressure and large unsupported spans can cause a membrane to fail in a shorter time than if only one of the conditions existed.

There are three modes of failure which are observed when microporous PTFE membranes are subjected to excessive conditions, such as the three conditions described above. First, when the membrane is pressurized across an unsupported span, the membrane may rupture in the middle of the span. This type of failure can be seen on both a macroscopic scale (greater than 1 millimeter) and on a microscopic scale (less than 1 millimeter). This type of failure will be referred to as an elongation failure. Second, the membrane may fail when the pressure of the fluid forces the membrane against a sharp edge or other irregularity in the supporting layer of the laminate. Such sharp points may be either in direct contact with the membrane or may "telegraph" indirectly through an intervening layer. This phenomenon of "telegraphing" is a special case of elongation due to localized bending strain around a sharp edge or point in the materials which contact the membrane; this type of failure will be referred to as a puncture failure. Third, the membrane may fail if a large portion of the strain is concentrated within a small portion of the membrane. In contrast, an advantageous situation is one in which there is a gradual transition from the point of support to the point of no support. This type of failure will be referred to as a strain relief failure. An example of this is the situation in which the strain due to deformation is concentrated at the perimeter at which the membrane is supported. For instance, if at the circumference where the membrane is supported across a circular aperture, there is a sharp transition from the flexible construction of the laminate to the rigid frame of the body of the device, there exists a condition which causes a localized higher concentration of strain in the membrane (due to the modulus mismatch between the rigid support and the flexible laminate support).

The time dependent nature of the failure of microporous hydrophobic membranes, such as failure due to the factors described above, results from the tendency of PTFE to creep under load. All plastics are, to some extent, viscoelastic. This is reflected in the stress-strain relationships of plastic materials. Under static load, the deformation and rupture behavior of plastics at any temperatures under all types of stresses is significantly affected by the time the material is under load. Irradiated microporous PTFE membranes are particularly low in ultimate elongation and, thus, particularly susceptible to failure involving reduced creep resistance. For this reason, irradiated devices incorporating microporous PTFE membranes which will be exposed to ionizing radiation must be critically designed to minimize all stresses which impact on the membrane.

For any given device and conditions of operation, there is a useful lifetime during which the microporous PTFE membrane will not fail under said conditions. When this time is exceeded by a certain amount, the membrane will eventually fail. After a device has been exposed to the levels of ionizing radiation typically employed in sterilizing procedures, this useful lifetime is significantly reduced. In some instances, the useful life is reduced to the point that the device is no longer acceptable for use in the intended service. The examples in this patent describe worst case situations in which thin, microporous PTFE membranes are exposed to both ionizing radiation and pressure and must maintain their integrity.

Deficiencies in performance after exposure to ionizing radiation similar to those described above also exist with respect to microporous hydrophobic membranes other than those composed of PTFE but to a lesser degree. The laminates of the preferred embodiments, described below, disclose compositions which do not have these deficiencies.

Thus, the composite comprises a microporous hydrophobic layer and one or more supporting layers which function to prevent transmission of mechanical stresses to the microporous hydrophobic layer. One such preferred composite construction comprises three layers in which the first layer prevents the excessive elongation of the composite (including the microporous hydrophobic membrane) by virtue of its stiffness and a second intermediary layer of a compliant material which prevents the transmission of forces due to the irregularities of the first layer to the third microporous membrane layer. The third layer is a microporous hydrophobic membrane. It is also advantageous if the first layer, or the construction of the device, acts to prevent the overall composite from conforming to sharp corners, such as at the rigid supporting edge of the device itself, or other areas of modulus mismatch, which would cause excessive concentrations of stresses on a small portion of the PTFE membrane.

Preferably, in the three or more layered constructions of this invention, the components are:

a) a woven or extruded porous sheet which has, after irradiation, an elongation of less than 25% elongation after 100 hours under a load of 2.0 pounds per inch, which serves to prevent the microporous layer from bearing excessive mechanical stresses by virtue of the stiffness that this layer contributes to the overall laminate;

b) a nonwoven material, or other compliant, porous and substantially smooth material, preferably with a basis weight of between 1.0 and 6.0 ounces per square yard, which acts as a buffer layer between the layer (a) and the layer (c) by diffusing the stresses between these layers;

c) a microporous hydrophobic layer, with a nominal pore size preferably between 0.01 and 100 micrometers and with a thickness preferably between 2 and 250 micrometers, which serves as a hydrophobic barrier to water, aqueous solutions and mixtures, as well as microscopic and macroscopic contamination, but allows the passage of air and other gases, and the properties of the layers are such that the laminates are, after exposure to 5 Megarad of ionizing radiation, capable of withstanding 20 psig pressure for 100 hours in the Pressurization Test, described herein, without rupturing. It is necessary that the surface of the metal or polymeric material be completely free from burrs, sharp edges on the filaments and bends of small radius.

Basis weight refers to the nominal weight of a square yard of material as determined by weighing a sample of known area and dividing the weight by the area in ounces and yards, respectively. Maximum pore sizes are determined by the Bubble Point Test, as described in ASTM F-316 using methanol. The nominal pore sizes which are used to describe the membranes are approximately the pore size corresponding to the mean flow pore pressure.

As a more preferred embodiment, the multilayer composite of this invention comprises at least three layers with the components arranged in this order:

a) a woven polyester screen which is preferably woven from filaments which are about 125 micrometers in diameter, and is preferably of a square or twill weave pattern of about 120 filaments per inch;

b) a polyester nonwoven material, which preferably is spunbonded from 3 denier or smaller filaments and preferably has a basis weight of 1 to 6 ounces per square yard;

c) a microporous PTFE membrane which has a nominal pore size of 0.01 to 100 micrometers and a thickness of between 2 to 250 micrometers, and the properties of the layers are such that the composite, after exposure to 5 Megarad of ionizing radiation, is capable of withstanding 20 psig pressure for 100 hours in the Pressurization Test without rupturing.

Still another embodiment is a multilayer composite comprising a microporous PTFE membrane which is supported on both sides by one or more of the previously described supporting layers. In this composite, the supporting layers are on each side of the microporous PTFE membrane and they may be identical or different.

The layers of the composites may be joined together, for example, with a hot melt adhesive, such as a polyester powder, which is coated onto the layers to be laminated, then heated near or above its melt point temperature and the layers are subjected to pressure to ensure a bond is formed. This process can be accomplished in two steps: first, the (a) and (b) layers are laminated; then, subsequent layers are joined to said laminate in the same fashion. The adhesive, either hot melt or solvent, may be applied either randomly or in regular patterns. Alternatively, the layers may not be joined by adhesives but simply restrained in place by any of the methods described in the definition of devices.

The present invention discloses a method of making multilayer microporous PTFE composites and devices containing such composites, for use in applications which involve exposure to ionizing radiation. Said composites and devices can be utilized in more adverse conditions (such as under higher pressure, longer periods under pressure, or after ionizing radiation, or all of the above) than existing composites or devices. Since microporous PTFE is the component of the composite most susceptible to failure due to ionizing radiation, composites or devices with improved durability can be made by observing the design criteria, described herein, which minimize the exposure of the microporous PTFE to the mechanical stresses which can cause it to fail.

The composites, and devices containing the composites, of this invention will have utility in a variety of applications. The said composites and devices will be especially useful in applications which require exposure to ionizing radiation, preferably in the range of 0.5 to 10.0 Megarad. Said composites and devices are of particular utility in venting applications including, but not limited to, in-line intravenous solution filter vents, IV spike vents, transducer protectors, urine bag vents, colostomy bag vents, vented blood gas syringes, burette vents, vents for diagnostic test apparatus such as multiwell diagnostic test strips, vents on devices for chest, peritoneal or other cavity drainage, catheter vents, ear plug vents, cap vents and cell growth container vents. Said composites and devices will also find utility in applications as filter/separators including, but not limited to, respirator humidifiers, oxygenators, suction canister filters, in-line vacuum filters, air sampling filters, medical bed filters, or filters in carbon dioxide generators. The vents or filters may be of any shape; in many of the applications listed above, the membrane or laminate is commonly in the form of a flat sheet. It is also possible to apply the teachings of this patent to other shapes of microporous hydrophobic membranes and their laminates, such as cylindrical or pleated sheet configurations. Additionally, these principles of design and construction can be applied to other implantable medical devices which are subjected to pressure in their applications. Devices such as vascular grafts, patches, dental implants and wound dressings could be made to withstand higher pressures by using the principles of lamination as a method of reinforcement. Additionally, it will be obvious to one skilled in the art that the principles of construction taught in this patent can be utilized to make laminates and devices which are not subjected to ionizing radiation but are to be used at higher pressures and/or for longer periods of time than existing laminates or devices. It is also obvious that the principles explained in this patent can be used in applications where other materials require additional support to function effectively at sustained pressures or after irradiation. Such materials include, but are not limited to, full density PTFE, filled PTFE, expanded and impregnated PTFE, full density sheeting or microporous sheeting of other polymers such as polyethylene, polypropylene or other fluoropolymers.

Devices

Figure 2:
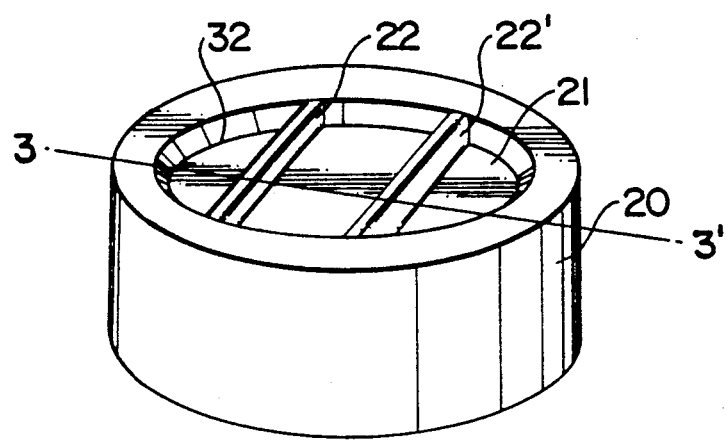
FIG. 2 is a drawing of a device of this invention with two supporting members.

FIG. 2 shows a device of the invention comprising a cylindrical device (20) which restrains a circular composite (21). There are supporting cross members (22 and 22') which provide additional support across a diameter of the composite (21). The line 3—3' represents the plane of the cross section shown in FIG. 3.

Figure 3:
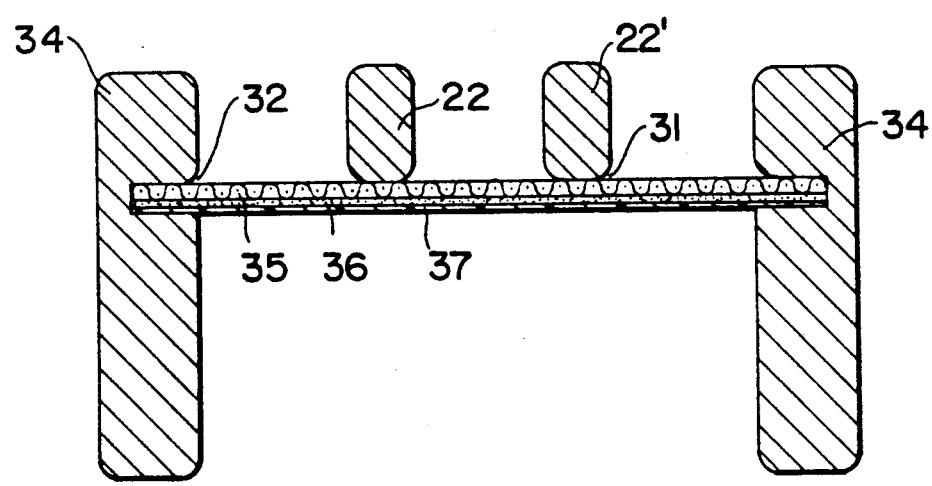
FIG. 3 shows a cross sectional view of the device in FIG. 2.

FIG. 3 is a cross sectional view of the device in FIG. 2 which shows the placement of the rounded edges (31 and 32) of the cross members (22 and 22') and the body of the device (34), respectively. Devices can also be constructed with various numbers of cross members to provide more support for the composites. Devices can also be constructed with a backing plate which contains circular holes of such diameter that the composite is sufficiently supported. The figure also shows a cross sectional view of the composite. The composite has a layer of screen of low elongation (35), a layer of compliant material (36) and a layer of microporous hydrophobic membrane (37). The composite is oriented with the microporous hydrophobic membrane adjacent to the pressurized fluid.

The examples below illustrate composites of this invention in which the supporting layers are made from selected materials. It is obvious to one skilled in the art that other materials which possess similar properties can be used as the supporting layer or layers without departing from the spirit of this invention. For instance, other metal screens, such as those made from brass, nickel, Monel, etc., could also be used. Glass screens with the appropriate physical properties could also be used. Polymeric screens could be made from other polymers, such as polyamides, polyaramids, polyimides, or polybenzimidazoles. The compliant intermediary layer could be made of other materials, such as cellulosics, polyamides, polyimides, polyesters, polyurethanes, or polyolefins of nonwoven or other construction. The compliant layer can have a basis weight of between 1 and 15 ounces per square yard, preferably between 1 and 6 ounces per square yard.

Pressurization Test

The composites of this invention can conveniently be tested under conditions which simulate actual conditions of use in pressurizable devices, such as a vent which allows the passage of air and functions as an aqueous barrier. Referring to FIG. 1, the testing device comprises a hollow metal cylinder (10) which serves as a reservoir for the challenge fluid (11) which will be tested. The cylinder is constructed such that the top surface (12) is machined to accept an O-ring (13) to seal the sample laminate (14) to prevent the leakage of the test solution. The cylinder is also fitted with a means of pressurizing the solution by means of pressurized air (15) which is controlled by a regulator (16). The laminate is sealed by compressing the laminate between an O-ring (which seats against the metal cylinder) and an acrylic disk (17) with a hole in the middle (18) which is secured to the metal cylinder by means of bolts (19) or other clamping devices.

The acrylic disk has been modified so that the test closely simulates the actual conditions of the device in which the laminate will ultimately be used. The acrylic material is a rigid material that simulates the actual material into which the laminate is insert molded or otherwise restrained. The acrylic disks were machined from ¼ inch slab stock with a ⅜ inch hole drilled in the center and chamfered to an included angle of 82° and finished sanded with 600 grit paper to insure the absence of sharp edges. To simulate the actual conditions of use, the test is performed with a solution typical of those used in intravenous (IV) applications. Such a solution consists of 25% dextrose, 4% amino acids and 1% multivitamin solution. The testing procedure includes exposing the sample to 5 Megarad of ionizing radiation, mounting the sample, pressurizing the fluid to a predetermined pressure and maintaining the pressure for 100 hours or until the sample leaks, whichever comes first.

The test results are expressed as the time a sample has been pressurized prior to failure, or the time of discontinuation of testing a sample which has not failed, usually 100 or 200 hours. In the following Tables, the test results are tabulated as the useful lifetimes at the various pressures at which the laminate was tested. It is also possible to use high flow membranes, that is, membranes which have water entry pressures lower than 20 psig. In these cases the laminates of this invention are useful in preventing the failure of the membrane at pressures less than the water entry pressure.

EXAMPLE 1

A three layer laminate was made with the components in the following order:

a) a woven polyester screen, manufactured by Tetko, Inc. designated as PeCap ® polyester screen, product number 7-130/38. This is a square weave product that has a mesh count of 121 filaments per inch; the filaments are 135 micrometers in diameter; the screen thickness is 150 micrometers and it has a basis weight of 2.0 ounces per square yard. The openings are 130 micrometers square and the percent open area is 38%;

b) A polyester nonwoven material manufactured by Reemay, Inc. designated as Reemay 2295. This is a spunbonded product made from 2.2 denier polyester filaments; it has a basis weight of 2.95 ounces per square yard;

c) A microporous polytetrafluoroethylene (PTFE) material which has a nominal pore size of 0.02 micrometers and a thickness of between 75 and 100 micrometers, manufactured by W. L. Gore and Associates, Inc.

These three layers were joined together by hot melt bonding with a low melting polyester powder manufactured by Goodyear, Inc. The powder was coated onto the layer (a), layer (b) was layered on the powdered side, then the composite was heated above the melt point of the polyester powder (120° C.), and subjected to pressure to ensure a sufficient bond between the individual layers was formed. This process was repeated, now putting the powder on the surface of layer (b) and joining layer (c) to it with heat and pressure.

The laminate was tested as described in the Pressurization Test and the results are shown in Table I.

EXAMPLE 2

A combination of two layers was made with the following components:

(a) a woven screen manufactured by Tetko, Inc. which was made from 0.004 inch diameter stainless steel wire in a twill square weave pattern of 120 filaments per inch having openings of 0.0043 inches square and 26.8% open area; this material has a basis weight of approximately 18 ounces per square yard;

(b) a microporous PTFE material which has a nominal pore size of 0.02 micrometers and a thickness of between 75 and 100 micrometers, manufactured by W. L. Gore and Associates, Inc.

The combination of layers were restrained by the pressure of the O-ring seal used in the Pressurization Test device. This combination of layers was tested as described in the Pressurization Test and the results are shown in Table I.

EXAMPLE 3

A combination of three layers was made with the following components:

(a) a sheet of extruded screening manufactured by Conwed, Inc. characterized by a rectangular pattern of 30 by 34 strands per inch which are made from polypropylene. The two sides of the screening used herein had different degrees of smoothness. The smoother side was placed against the microporous PTFE layer;

b) a polyester nonwoven material manufactured by Reemay, Inc. designated as Reemay 2295. This is a spunbonded product made from 2.2 denier polyester filaments; it has a basis weight of 2.95 ounces per square yard;

c) a microporous PTFE material which has a nominal pore size of 0.02 micrometers and a thickness of between 75 and 100 micrometers, manufactured by W. L. Gore and Associates, Inc. The combination of layers were restrained by the pressure of the O-ring seal used in the Pressurization Test device.

EXAMPLE 4

A combination of five layers which provides support on both sides of the microporous hydrophobic membrane comprises the following layers:
(a) a woven material,
(b) a nonwoven material, (c) a microporous PTFE membrane,
(d) a nonwoven material,
(e) a woven material.

These materials were those described in Example 1. The microporous PTFE membrane of this construction is protected from pressurization in both directions.

EXAMPLE 5

A combination of three layers which provides support on both sides of the microporous hydrophobic membrane comprises the following layers:
(a) a woven metal material,
(b) a microporous PTFE membrane, and
(c) a woven metal material.

These materials were those described in Example 2. The microporous PTFE membrane of this construction is protected from pressurization in both directions.

COMPARISON EXAMPLE

The comparison example is a commercially available laminate. This laminate consists of three layers, in the following order:

(a) a woven polyester screen woven from filaments of 135 micrometer diameter in a square weave pattern which has 121 filaments per inch;

(b) a spunbonded polyester nonwoven material made from 2.2 denier filaments which has a basis weight of 0.75 ounces per square yard;

(c) a microporous PTFE membrane which has a nominal pore size of 0.02 micrometers and a thickness of between 75 and 100 micrometers.

The laminate was tested as described in the Pressurization Test and the results are shown in Table I. It is not acceptable for use in radiation sterilized applications.

Table I summarizes the performance data of the above composite examples. The Table includes the comparison example as a reference point for comparing the improvement of the examples. Prior to testing, all samples were exposed to 5.0 Megarad of gamma irradiation. The numbers in the table are the average times to failure or cessation of testing (in hours) at a given pressure (in psig). Failure is defined as the time at rupture, that is, the time at which the composite no longer was a functional barrier to the solution and the solution was observed leaking through the composite in the Pressurization Test.

All laminates were tested under the same conditions in the Pressurization Test. Thus, the composite data demonstrates the effects of different composite constructions.

In the Table, the symbol ">" indicates that at the specified time the sample had not failed and that the test was discontinued at that point. The symbol "—" indicates that, although the laminate was not tested at that pressure, the sample had not leaked at 100 hours when tested at a higher pressure. It is obvious that, if the samples were tested at these conditions, times to failure of much greater than 100 hours would be observed. The data points shown in the Table are taken from graphs of time to rupture failure plotted against pressure.

TABLE I

| RESULTS OF COMPOSITES TESTING TIME TO FAILURE (hours) | | | | |
|---|---|---|---|---|
| Composites* | 10 psig | 30 psig | 50 psig | 70 psig |
| Comparison | 100 | 1 | <0.5 | <0.5 |
| Example 1 | — | — | >100 | 35 |

TABLE I-continued

| RESULTS OF COMPOSITES TESTING TIME TO FAILURE (hours) | | | | |
|---|---|---|---|---|
| Composites* | 10 psig | 30 psig | 50 psig | 70 psig |
| Example 2 | — | >200 | >50 | not tested |

*These laminates and combinations were tested at a ⅛ inch diameter opening.

The Table indicates that irradiated composites can be substantially improved by the disclosed modifications. Table I indicates that the improvements of the two layer combination of layers, Example 2, result in a greater than one hundred-fold improvement in the useful life of the laminate at 30 psig pressure. Table I also indicates that the improvements of the three layer laminate, Example 1, result in a greater than one hundred-fold improvement in the useful life of the laminate at 50 psig pressure.

We claim:

1. A radiation-resistant polytetrafluoroethylene composite comprising:
   (a) a layer of woven metal material which has an elongation of less than 25% after 100 hours under a load of 2.0 pounds per inch, and
   (b) a layer of microporous hydrophobic polytetrafluoroethylene membrane,
   wherein the properties of the layers are such that the composite is capable of withstanding either (i) at least 20 pounds per square inch of pressure, or (ii) the water entry pressure of the membrane, whichever is less, for 100 hours in the Pressurization Test without rupturing.

2. A composite of claim 1 in the form of a laminate.

3. A composite of claim 1 wherein the material of the layer (a) is a woven metal screen.

4. A filtration device containing the composite of claim 1.

5. Process for preparing a laminated composite of claim 1 which comprises bonding layers (a) and (b) together with a hot melt bonding adhesive.

6. Process for irradiating an unirradiated composite of claim 1 which comprises subjecting the composite to ionizing radiation of between 0.5 to 10 Megarad.

7. A radiation resistant polytetrafluoroethylene composite comprising:
   (a) a layer of an synthetic organic polymeric material having an elongation of less than 25% elongation after 100 hours under a load of 2.0 pounds per inch, and
   (b) a middle layer of a compliant synthetic organic polymeric material that is porous and substantially smooth, and has a basis weight of between 1 and 6 ounces per square yard, and
   (c) a layer of microporous hydrophobic polytetrafluoroethylene membrane,
   wherein the properties of the layers are such that the composite is capable of withstanding either (i) at least 20 pounds per square inch of pressure, or (ii) the water entry pressure of the membrane, whichever is less, for 100 hours in the Pressurization Test without rupturing.

8. A composite of claim 7 in the form of a laminate.

9. A composite of claim 7 wherein layer (a) is a woven polyester screen, layer (b) is a nonwoven of fine polyester filaments which has a basis weight of 1 to 6 ounces per square yard, and layer (c) is a microporous polytetrafluoroethylene membrane which has a pore size of between about 0.01 to 100 micrometers and a thickness of between 2 to 250 micrometers.

10. A filtration device containing the composite of claim 7.

11. The filtration device of claim 10 wherein the device contains rounded edges so as to provide strain relief to the filtration medium.

12. The filtration device of claim 10 wherein the device contains one or more additional cross members which have rounded supporting edges so as to provide strain relief to the filtration medium.

13. Process for preparing a laminated composite of claim 7 which comprises bonding the layers together with a hot melt bonding adhesive.

14. Process for irradiating an unirradiated composite of claim 7 which comprises subjecting the laminate to ionizing radiation of between 0.5 to 10 Megarad.

* * * * *